(12) United States Patent
Filliers et al.

(10) Patent No.: US 8,440,863 B2
(45) Date of Patent: May 14, 2013

(54) PREPARATION OF (2R,3R)-3-(3-METHOXYPHENYL)-N,N,2-TRIMETHYLPENTANAMINE

(75) Inventors: Walter Ferdinand Maria Filliers, Vremde (BE); Rudy Laurent Maria Broeckx, Turnhout (BE)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 13/397,186

(22) Filed: Feb. 15, 2012

(65) Prior Publication Data

US 2012/0142970 A1 Jun. 7, 2012

Related U.S. Application Data

(62) Division of application No. 12/374,894, filed as application No. PCT/EP2007/057559 on Jul. 23, 2007, now Pat. No. 8,138,376.

(30) Foreign Application Priority Data

Jul. 24, 2006 (EP) .................................. 06117708

(51) Int. Cl.
*C07C 215/00* (2006.01)

(52) U.S. Cl.
USPC ........... 564/443; 564/355; 564/356; 564/374; 514/653; 514/533; 514/345

(58) Field of Classification Search ....................... None
See application file for complete search history.

(56) References Cited

U.S. PATENT DOCUMENTS

| | | | |
|---|---|---|---|
| 6,248,737 B1 * | 6/2001 | Buschmann et al. | 514/231.8 |
| 6,344,558 B1 * | 2/2002 | Buschmann et al. | 544/86 |
| 2009/0326271 A1 * | 12/2009 | Hell | 564/344 |

OTHER PUBLICATIONS

Spalva, E.A., Database CA, Chemical Abstracts Service, Columbus, OH, US; "Relations between structure and anesthetic activity of some esters of aralkanols", Database accession No. 1964: 85583 abstract & Framakologiya I. Toksikologiya (Moscow), 26 (5), 606-11, 1963.

* cited by examiner

*Primary Examiner* — Sudhakar Katakam

(57) ABSTRACT

The present invention relates to an improved process for the preparation of (2R,3R)-3-(3-methoxyphenyl)-N,N,2-trimethylpentanamine which is an intermediate for the preparation of the analgesic tapentadol.

3 Claims, No Drawings

PREPARATION OF (2R,3R)-3-(3-METHOXYPHENYL)-N,N,2-TRIMETHYLPENTANAMINE

CROSS REFERENCE TO RELATED APPLICATIONS

This divisional application claims the benefit of parent application Ser. No. 12/374,894, filed 23 Jan. 2009, now U.S. Pat. No. 8,138,376 which is the national stage of Application No. PCT/EP2007/057559, filed 23 Jul. 2007, which application claims priority from PCT/EP06117708.5 filed 24 Jul. 2006.

The present invention relates to an improved process for the preparation of (2R,3R)-3-(3-methoxyphenyl)-N,N,2-trimethylpentanamine which is an intermediate for the preparation of the analgesic tapentadol.

Tapentadol is the INN (International Non-proprietary Name) of 3-[(1R,2R)-3-(dimethylamino)-1-ethyl-2-methylpropyl]phenol monohydrochloride which compound is represented by the formula:

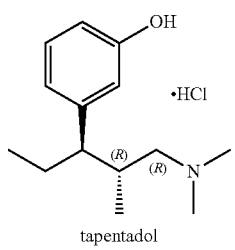

tapentadol

The chemical structure of tapentadol has been disclosed in EP-A-0,693,475 as compound (+21). The synthesis of tapentadol is described in Example 1 and Example 24 steps 1 to 3 and is outlined below using the compound numbers as mentioned in said EP-A-0,693,475.

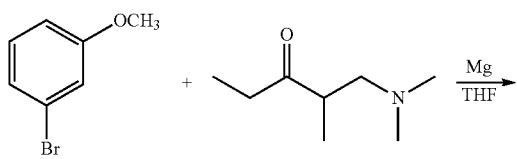

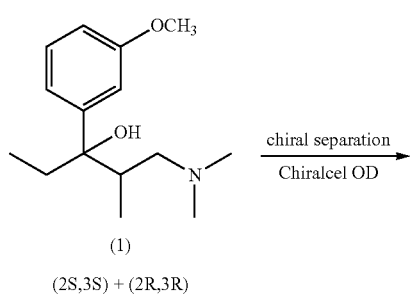

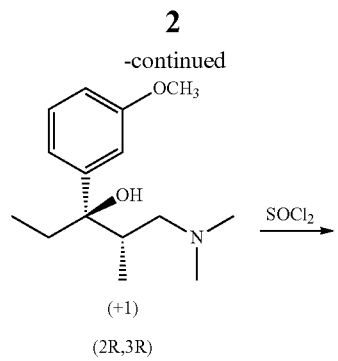

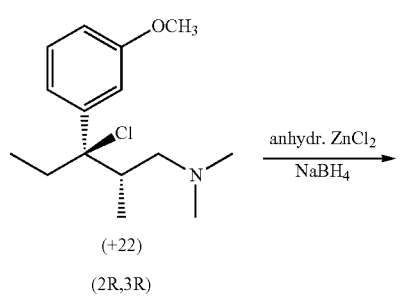

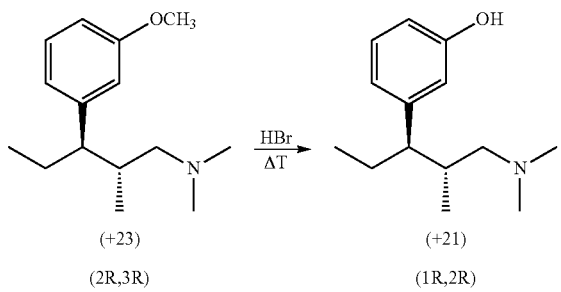

The synthetic precursor of tapentadol in the above scheme is (2R,3R)-3-(3-methoxy-phenyl)-N,N,2-trimethylpentanamine (intermediate (+23) in the above scheme) which can be obtained by removing the tertiary hydroxy group of (2S,3R)-1-(dimethylamino)-3-(3-methoxyphenyl)-2-methyl-3-pentanol by consecutive conversion into the corresponding halogenide with thionyl chloride and subsequent removal of the Cl by treatment with zinc borohydride, zinc cyanoborohydride and/or tin cyanoborohydride. This procedure has the disadvantage that the halogenide compound is prepared using an excess amount of thionyl chloride which is an aggressive chlorinating agent. Moreover the hydrogenation reagents such as zinc borohydride, zinc cyanoborohydride and tin cyanoborohydride present a considerable fire and health danger when used on an industrial scale.

WO-2004/108658 discloses an alternative process for obtaining (2R,3R)-3-(3-methoxy-phenyl)-N,N,2-trimethylpentanamine by converting (2S,3S)-1-(dimethylamino)-3-(3-methoxyphenyl)-2-methyl-3-pentanol into a mixture of (2R,3R) and (2R,3S)-3-(3-methoxyphenyl)-N,N,2-trimethylpentanamine as outlined below.

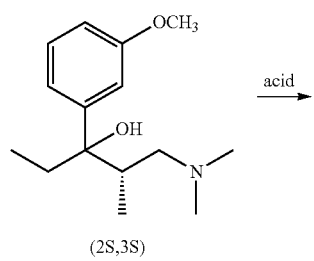

(2S,3S) → acid

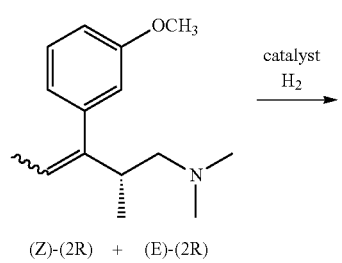

(Z)-(2R) + (E)-(2R)

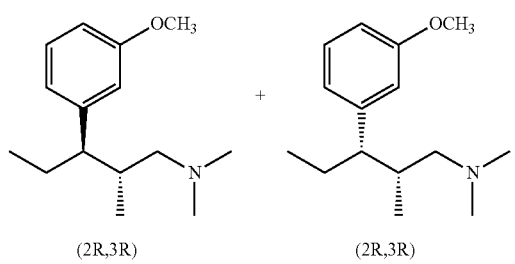

(2R,3R) + (2R,3R)

The resulting mixture of (2R,3R) and (2R,3S)-3-(3-methoxyphenyl)-N,N,2-trimethyl-pentanamine has to be separated into its individual stereoisomers in order to obtain the desired (2R,3R)-3-(3-methoxyphenyl)-N,N,2-trimethylpentanamine, which can then be converted into tapentadol by e.g. heating with concentrated hydrobromic acid as described in EP-A-0,693,475.

WO-2005/000788 discloses an alternative process for obtaining (2R,3R)-3-(3-methoxy-phenyl)-N,N,2-trimethyl-pentanamine by converting (2S,3S)-1-(dimethylamino)-3-(3-methoxyphenyl)-2-methyl-3-pentanol into a mixture of (2R,3R) and (2R,3S)-3-(3-methoxyphenyl)-N,N,2-trimethylpentanamine as outlined below.

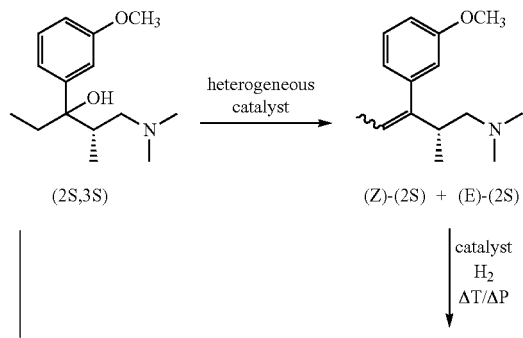

(2S,3S) → heterogeneous catalyst → (Z)-(2S) + (E)-(2S)

catalyst H₂ ΔT/ΔP

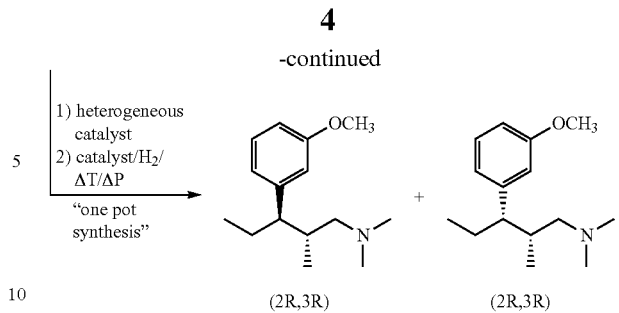

1) heterogeneous catalyst
2) catalyst/H₂/ΔT/ΔP
"one pot synthesis"

(2R,3R) + (2R,3R)

The resulting mixture of (2R,3R) and (2R,3S)-3-(3-methoxyphenyl)-N,N,2-trimethylpentanamine has to be separated into its individual stereoisomers in order to obtain the desired (2R,3R)-3-(3-methoxyphenyl)-N,N,2-trimethylpentanamine, which can then be converted into tapentadol by e.g. heating with concentrated hydrobromic acid as described in EP-A-0,693,475.

Both alternative processes of WO-2004/108658 and WO-2005/00078 have the disadvantage that [3-(3-methoxyphenyl)-N,N,2-trimethylpentanamine is obtained as a mixture of the (2R,3R) and (2R,3S) stereoisomers which have to be separated in order to obtain the desired (2R,3R) stereoisomer. The undesired (2R,3S) stereoisomer cannot be converted into the desired (2R,3R) stereoisomer and has to be disposed of as chemical waste, which is economically undesirable for any industrial scale production.

The object of the present invention is to provide an improved method for the synthesis of (2R,3R)-3-(3-methoxyphenyl)-N,N,2-trimethylpentanamine which is more convenient and more efficient than the previously known methods.

The present invention achieves this object by providing an improved process for the preparation of (2R,3R)-3-(3-methoxyphenyl)-N,N,2-trimethylpentanamine, or an acid addition salt thereof, which is characterized by the steps of a) acylating (2S,3R)-1-(dimethylamino)-3-(3-methoxyphenyl)-2-methyl-3-pentanol

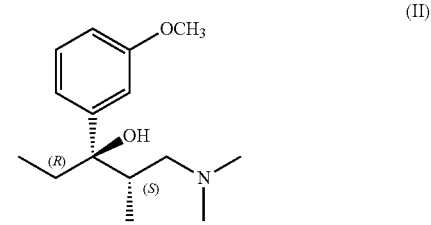

(II)

with an acylating agent;

b) stereoselective hydrogenolysis of the thus obtained compound (III)

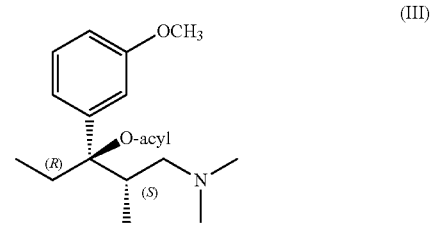

(III)

using a suitable catalyst in a reaction-inert solvent in the presence of hydrogen; and c) optionally converting the thus obtained (2R,3R)-3-(3-methoxyphenyl)-N,N,2-trimethylpentanamine

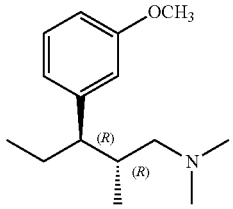

(IV)

into an acid addition salt.

The acylating agent of step a) is an organic acyl halide or organic acid anhydride selected from acetic anhydride, acetyl chloride, trifluoroacetic anhydride, chloroacetic anhydride, chloro acetylchloride, dichloroacetic anhydride, trichloroacetic anhydride, benzoic anhydride, benzoyl chloride, phthalic anhydride, phtaloyl dichloride, terephthaloyldichloride, succinic anhydride, succinyl chloride, ethyl oxalyl chloride, methyl oxalyl chloride, Meldrum's acid, ethyl chloroformate, methylchloroformate, acetylsalicyloyl chloride, or any other suitable acylating agent.

The acylation reaction of step a) may be performed in the presence of a suitable base, such as e.g. sodium carbonate, potassium carbonate or triethylamine, to capture the acid liberated during the reaction The catalyst of step b) is selected from a palladium catalyst, or any other suitable catalyst such as e.g. Raney nickel, platinum, platinum on carbon, ruthenium or rhodium on carbon.

The palladium (Pd) catalyst may be a homogeneous Pd catalyst, such as for example Pd(OAc)$_2$, PdCl$_2$, Pd(PPh$_3$)$_4$, Pd(PPh$_3$)$_2$Cl$_2$, Pd$_2$(dba)$_3$ (tris(dibenzylidene acetone) dipalladium), palladium thiomethylphenylglutaramide metallacycle and the like, or a heterogeneous Pd catalyst, such as for example palladium on charcoal, palladium on metal oxides, palladium on zeolites. Preferably, the palladium catalyst is a heterogeneous Pd catalyst, more preferably palladium on charcoal or palladium on carbon (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

The reaction-inert solvent of step b) is selected from diethyl ether, tetrahydrofuran, 2-methyltetrahydrofuran or mixtures thereof.

In an embodiment of the present invention, steps a) and b) are executed as a "one pot synthesis" procedure.

The present invention also relates to novel compounds of formula (III)

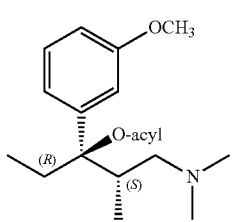

(III)

The acyl group in compounds of formula (III) represents CH$_3$—CO—, CF$_3$—CO—, CH$_2$Cl—CO—, CHCl$_2$—CO—, CCl$_3$—CO—, CH$_3$O—CO—CO—, CH$_3$O—CO—, CH$_3$CH$_2$O—CO—, CH$_3$CH$_2$O—CO—CO, phenyl-CO—, or meta-CH$_3$COO-phenyl-CO— when the acylating agent used to prepared the compounds of formula (III) as set out above is selected from acetic anhydride, acetyl chloride, trifluoroacetic anhydride, chloroacetic anhydride, chloro acetylchloride, dichloroacetic anhydride, trichloroacetic anhydride, methyl oxalyl chloride, ethyl oxalyl chloride, methyl chloroformate, ethyl chloroformate, benzoic anhydride, benzoyl chloride, or acetylsalicyloyl chloride.

The starting material for the process of the present invention, i.e. (2S,3R)-1-(dimethylamino)-3-(3-methoxyphenyl)-2-methyl-3-pentanol (compound 4), was prepared by reacting (2S)-3-(dimethylamino)-1-(3-methoxyphenyl)-2-methyl-1-propanone (compound 3) with ethylmagnesium chloride in THF under Grignard reaction conditions.

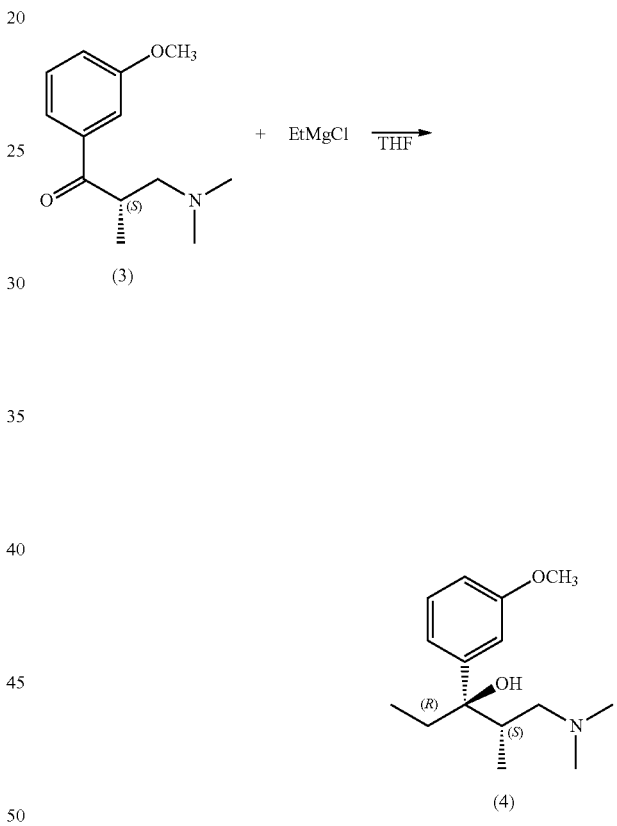

The reaction of the Grignard reagent with the ketone compound (3) introduces a second asymmetric carbon atom. The Grignard reaction of (2S)-3-(dimethylamino)-1-(3-methoxyphenyl)-2-methyl-1-propanone (compound 3) with an ethylmagnesium halide is highly stereospecific. The optical purity of the starting compound (3) was found to be 98.0%. Compound (4) was analysed to comprise 96.8% of the desired (2S,3R) enantiomer, less than 0.4% of the (2S,3S) enantiomer and 3.0% of the (2R,3S) enantiomer. Table 1 lists the stereoisomeric purity of the compound (4) when prepared as outlined above.

Compound (4) can be converted into compound (5) by acylating compound (4) with trifluoroacetic anhydride and subsequent hydrogenolysis over a palladium catalyst, using 2-methyltetrahydrofuran as a solvent, in a "one pot synthesis" procedure.

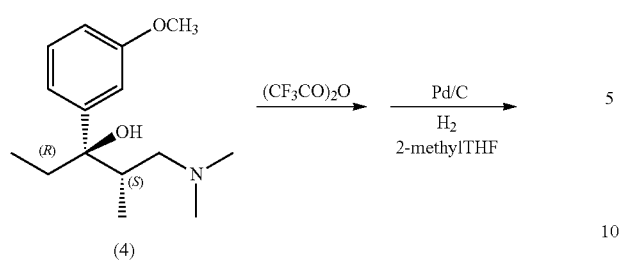

(4)

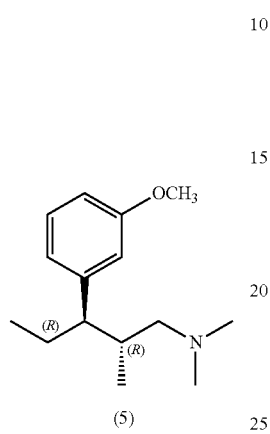

(5)

The optical purity of starting compound (4) was 96.8% enantiomer (2S,3R). It was found that hydrogenolysis after acylation of compound (4) is highly stereospecific to give the desired enantiomer (2R,3R)-enantiomer of compound (5) with an optical purity of 96.3%.

Additional salt formation of compound (5) further improves the optical purity of compound (5). For example, a diastereomeric excess of >99% was achieved by converting compound (5) to its hydrochloric acid salt compound (6) using 2-propanol as crystallization solvent.

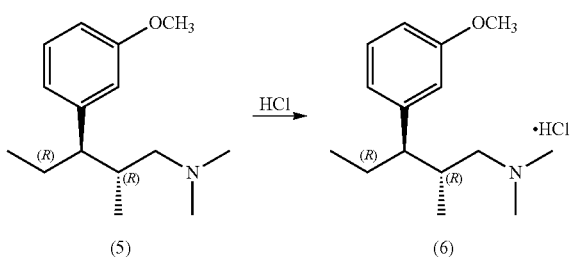

TABLE 1 stereoisomeric purity of compounds (4), (5) and (6)

| | Optical purity | | | |
| --- | --- | --- | --- | --- |
| | 2S-enantiomer: 98.0 | | 2R-enantiomer: 2.0 | |
| Compound (3) | 2S,3R | 2S,3S | 2R,3R | 2R,3S |
| Compound (4) | 96.8 | <0.4 | ~ | 3.0 |
| Compound (5) | ~ | <2.5 | 96.3 | 1.2 |
| Compound (6) | ~ | ~ | 99.7 | 0.3 |

EXPERIMENTAL PART

Example 1

Synthesis of 3-(dimethylamino)-1-(3-methoxyphenyl)-2-methyl-1-propanone (1)

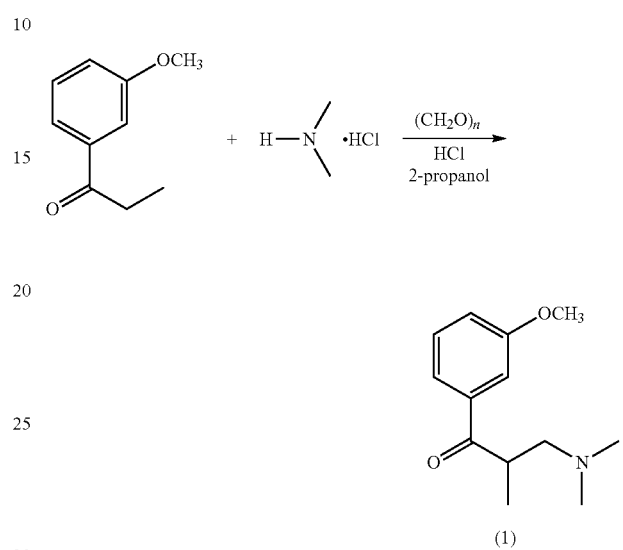

(1)

A mixture of 1-(3-methoxyphenyl)-1-propanone (240 g) in 2-propanol (584 ml) is stirred at ambient temperature. Dimethylamine hydrochloride (238.3 g) is added, followed by paraformaldehyde (109.5 g) and an aqueous HCl solution (26.5 ml, 35% w/w). The reaction mixture is heated to reflux temperature and stirred and refluxed for 5 hours. The reaction mixture is allowed to cool to 20° C., and water (730 ml) and toluene (146 ml) are added. The upper organic layer is discarded and an aqueous NaOH solution (50% w/w, 175.2 ml) is added to the water layer while stirring for 10 minutes and keeping the temperature below 25° C. After 10 minutes the layers are allowed to separate, the upper organic layer is isolated and washed with water (219 ml). The organic layer is isolated and concentrated to obtain 3-(dimethylamino)-1-(3-methoxyphenyl)-2-methyl-1-propanone as on oily residue (294.9 g).

Example 2

Synthesis and isolation of (2S)-3-(dimethylamino)-1-(3-methoxyphenyl)-2-methyl-1-propanone (3)

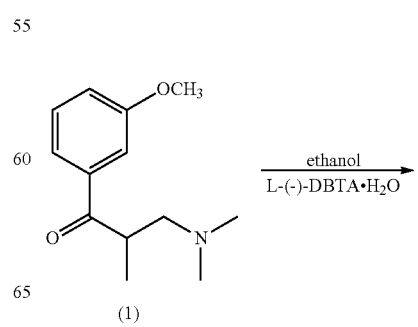

(1)

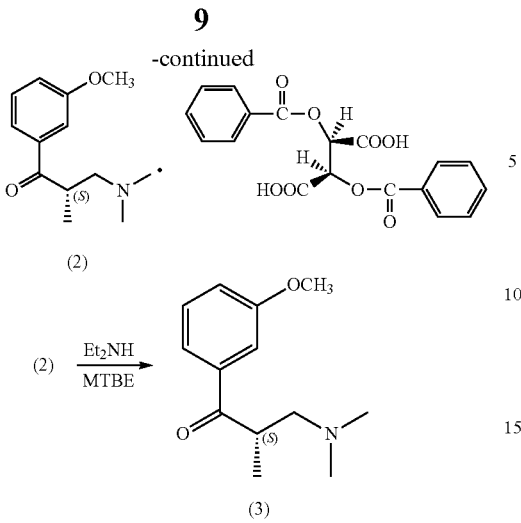

(2)

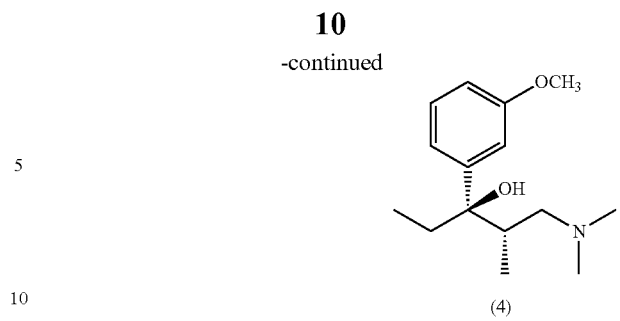

a) Compound (1) (114.7 g) in ethanol (50 ml) is added to a solution of L-(−)-dibenzoyl-tartaric acid monohydrate (188.2 g) in ethanol (950 ml) and the reaction mixture is warmed to 38° C. and stirred for 48 hours at 38° C. The reaction mixture is then allowed to cool to 22° C. and stirred for 14 hours at 22° C. The precipitate is filtered off, washed twice with ethanol (50 ml) and dried in vacuo at a temperature of 40° C., yielding compound (2) (207.5 g).

b) Compound (2) (202.9 g) is suspended in methyl-tert-butylether (1050 ml) and diethylamine (72.4 ml) is added. The suspension is stirred for 3 hours at ambient temperature and the precipitate is removed by filtration. The filtrate is concentrated under reduced pressure, yielding (2S)-3-(dimethylamino)-1-(3-methoxyphenyl)-2-methyl-1-propanone (3) as an oil (73.9 g).

An Alternative Procedure to Procedure b:

c) Compound (2) (312.8 g) is suspended in 2-methyltetrahydrofuran (405 ml) and water (540 ml). Aqueous NH$_4$OH (93 ml, 51% w/w) is added and the mixture is then allowed to stir for 30 minutes. The layers are separated and the isolated upper organic layer is washed with water (100 ml), then concentrated under reduced pressure, yielding (2S)-3-(dimethylamino)-1-(3-methoxyphenyl)-2-methyl-1-propanone (3) as a yellow oil (109.0 g).

Compound (3) prepared according to procedure of Example 2 typically has an enantiomeric purity of 97% or higher.

Example 3

Synthesis of (2S,3R)-1-(dimethylamino)-3-(3-methoxyphenyl)-2-methyl-3-pentanol (4)

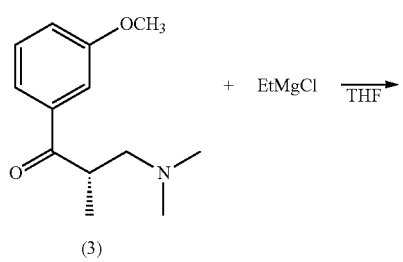

A solution of EtMgCl in THF (242 ml, 2M) was stirred and cooled to 2° C. Compound (3) (101.3 g, 0.44 mole) was slowly added over a period of 50 minutes while the temperature of the reaction mixture was kept below 25° C. The mixture was stirred for 3 hours at 22° C., then slowly quenched in a mixture of ice-water (352 ml) and acetic acid (63.9 ml). The mixture was stirred for 30 minutes at ambient temperature, then aqueous NH$_4$OH (98.8 ml, 51% w/w) was added and then allowed to stir for 10 minutes at ambient temperature.

The layers are separated and the isolated upper organic layer is then washed with water (44 ml), then concentrated under reduced pressure to dryness, yielding (2S,3R)-1-(dimethylamino)-3-(3-methoxyphenyl)-2-methyl-3-pentanol (4) as a yellow oil which solidifies upon standing at ambient temperature (112.0 g).

Compound (4) prepared according to the procedure of Example 4, comprises 96.8% of the desired (2S,3R) enantiomer, less than 0.4% of the (2S,3S) enantiomer and 3.0% of the (2R,3S) enantiomer.

Example 4

Synthesis of (2R,3R)-3-(3-methoxyphenyl)-N,N,2-trimethylpentanamine (5)

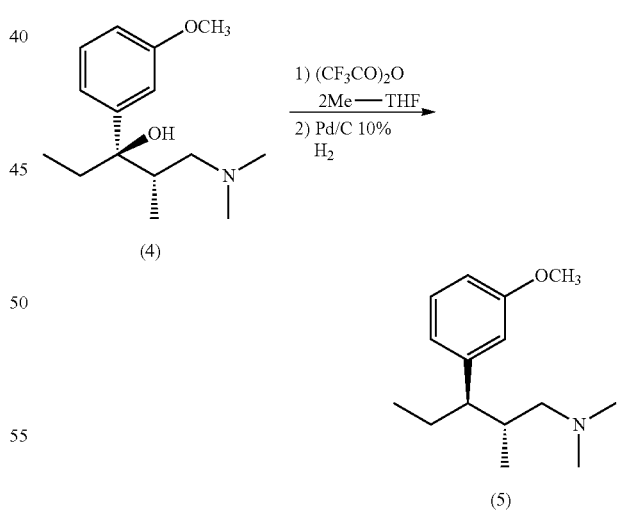

a) A solution of compound (4) (50.3 g) dissolved in 2-methyltetrahydrofuran (120 ml) was stirred and cooled to 5° C. Then trifluoroacetic anhydride (30.6 ml) was added slowly over a period of 10 minutes while the temperature of the reaction mixture was kept below 20° C. After addition, the reaction mixture was allowed to stir for 1 hour at 20° C.

b) Palladium 10% on activated carbon (50% wetted) (2.52 g) was added and the reaction mixture was stirred at 800 rpm and pressurized to 2 atmosphere (202.65 kPa) with hydrogen gas. The reaction mixture was heated to 40° C. and stirred for 4 hours at 40° C. The mixture was allowed to cool to 20° C. and filtered under nitrogen atmosphere. The filter was washed with 2-methyltetrahydrofuran (10 ml). Water (160 ml) was added to the filtrate and the mixture was stirred, then an aqueous NaOH solution (28.6 ml, 50% w/w) was added over a period of 10 minutes while the temperature was kept below 20° C. The organic and water layer were allowed to separate, the organic layer was isolated and washed with water (50 ml), and concentrated under reduced pressure to dryness, yielding (2R,3R)-3-(3-methoxyphenyl)-N,N,2-trimethyl-pentanamine (5) as a colourless oil (46.10 g).

Compound (5) prepared according to the procedure of Example 5 comprises 96.3% of the desired (2R,3R) enantiomer, 2.5% of the (2S,3S) enantiomer and 1.2% of the (2R,3S) enantiomer.

Using an analogous procedure as described in a) but replacing trifluoroacetic anhydride with acetyl chloride or ethyl oxalyl chloride and adding triethylamine to the reaction mixture, yielded compounds (7) and (8) respectively. Said compounds (7) and (8) were converted into compound (8) using the above procedure b).

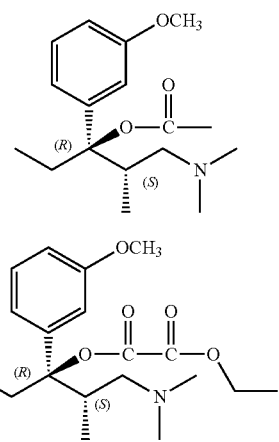

(7)

(8)

Example 5

Synthesis of (2R,3R)-3-(3-methoxyphenyl)-N,N,2-trimethylpentanamine monohydrochloride (6)

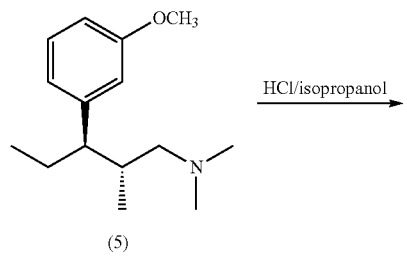

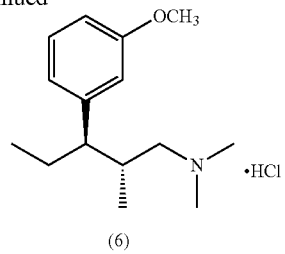

(6)

Compound (5) (23.0 g) was dissolved in 2-propanol (50 ml) and stirred at ambient temperature. Then a solution of HCl in 2-propanol (20.3 g, 17.9% w/w) was added slowly over a period of 5 minutes. The mixture was seeded with compound (6) (10 mg) and the reaction mixture was allowed to stir at ambient temperature for 1 hour. The mixture was cooled to a temperature of 0° C. and stirred for 4 hours. The precipitate was filtered off, washed with 2-propanol (5 ml) and dried under vacuo, yielding (2R,3R)-3-(3-methoxyphenyl)-N,N,2-trimethylpentanamine monohydrochloride (6) as a white solid (22.9 g).

Compound (6) prepared according to the procedure of Example 6 comprises 99.7% of the desired (2R,3R) enantiomer, and 0.3% of the (2R,3S) enantiomer.

The invention claimed is:

1. A compound of formula (III) wherein acyl represents $CF_3$—CO—, $CH_2Cl$—CO—, $CHCl_2$—CO—, $CCl_3$—CO—, $CH_3O$—CO—, $CH_3CH_2O$—CO—, $CH_3O$—CO—CO, $CH_3CH_2O$—CO—CO—, phenyl-CO—, or meta-$CH_3COO$-phenyl-CO—,

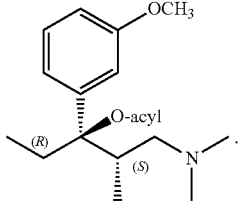

2. A compound of formula (III) as claimed in claim 1 wherein acyl represents $CF_3$—CO—.

3. A compound of formula (III) as claimed in claim 1 wherein acyl represents $CH_3CH_2O$—CO—CO—.

* * * * *